United States Patent [19]

Theodoropulos

[11] Patent Number: 5,118,499
[45] Date of Patent: Jun. 2, 1992

[54] QUINOLINE POLYMERS, THEIR CHELATES AND PROCESS OF PREPARATION AND USE

[76] Inventor: Spyros Theodoropulos, 2964 Hickory St., Yorktown Heights, N.Y. 10598

[21] Appl. No.: 717,368

[22] Filed: Jun. 19, 1991

[51] Int. Cl.$^5$ .................. A61K 43/00; A61K 31/74
[52] U.S. Cl. ........................... 424/78.23; 252/301.35; 252/301.36; 424/1.1; 528/62; 525/370
[58] Field of Search ............... 424/78; 252/301.35, 252/301.36

[56] References Cited

U.S. PATENT DOCUMENTS 3,193,536 7/1965 Wagner ..................... 252/301.35
4,931,553 6/1990 Gill ............................... 424/78

Primary Examiner—Thurman K. Page
Assistant Examiner—Raj Bawa

[57] ABSTRACT

Quinoline polymers are provided which are conveniently prepared by the reaction of 2-amino-8-hydroxyquinolines and diisocyanates. The resulting polymeric compounds are then chelated with certain metal ions to provide chelates having utility in biological areas or in areas where the properties of the particular metal ion chelate can be utilized.

16 Claims, No Drawings

QUINOLINE POLYMERS, THEIR CHELATES AND PROCESS OF PREPARATION AND USE

BACKGROUND OF THE INVENTION

1) Field of the Invention

This invention relates, in general, to novel quinoline polymers, chelates thereof, and their preparation and use. In one aspect this invention is directed to quinoline polymers which are produced by reacting 2-aminomethyl-8-hydroxyquinolines and diisocyanates and reacting the resultant polymeric product with a metal salt. In another aspect, this invention is directed to methods of preparing quinoline polymers and their chelates with transition metal ions, and their use in application areas which exploit the fluorescence or radioactivity of such chelates. The chelates of this invention are particularly useful in in vivo therapeutic applications utilizing radioactivity, or fluorescent labeling utilizing incident light. In a further aspect, the invention is directed to chelates of quinoline polymers with radioactive metal ions and their use in the topical treatment of rheumatoid arthritis and cancer.

2) Background of the Related Art

It is known that chelating agents such as ethylenediaminetetraacetic acid (EDTA), 1,3-diketones, thiosemicarbazides, and aminothiols, among others, form chelates with metal ions. However, few of the known chelates exhibit fluorescence and few have been shown to form water insoluble chelates, making the latter suitable for topical treatments utilizing radioactivity.

Accordingly, one or more of the following objects will be achieved by the practice of the present invention. It is an object of this invention to provide quinoline polymers produced from 2-aminomethyl -8-hydroxyquinolines and diisocyanates which are capable of forming chelates with transition metal ions. Another object of this invention is to provide novel polymer chelates which will exhibit distinct fluorescence excitation and emission spectra corresponding to that of the specific metal ion which is chelated and wherein the chelates themselves are stable. It is a further object of the present invention to provide quinoline polymers which can be used for the preparation of chelates of radioactive metal ions. A still further object of this invention, is to provide stable polymeric chelates of radionuclides which are water insoluble, and are useful for the topical treatment of rheumatoidal arthritis and cancer. These and other objects will readily become apparent to those skilled in the art in the light of the teachings contained herein.

SUMMARY OF THE INVENTION

In its broad aspect, this invention is directed to polymers produced from 2-amino-8-hydroxyquinolines and diisocyanates, certain metal chelates of these polymers with transition metal ions, and to processes for their preparation and use. The present invention is particularly directed to the chelates of quinoline polymers with readioactive metals, which are water insoluble and well suited for topical treatment of of rheumatoidal arthritis in joints (synovial cavity), and cancer. Chelates of the quinoline polymers with rare earth metal ions will exhibit fluorescence upon exposure to incident light. Such chelates have application in fluorescent labeling, while chelates with radioactive metals have therapeutic applications. The complexes of quinoline polymers with radionuclides, for example, can be localized in in vivo areas wherein radioactivity confers therapeutic benefits.

DETAILED DESCRIPTION OF THE INVENTION

The quinoline polymers employed in the present invention have the following recurring units:

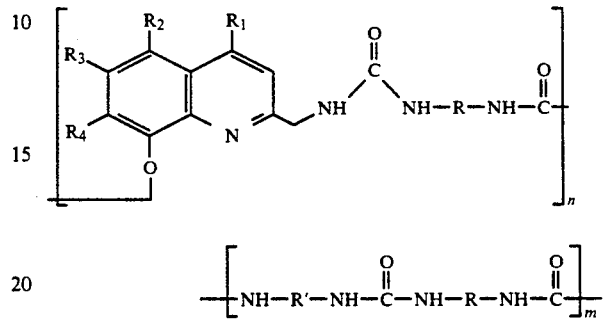

wherein n is an integer having a value of up to 10,000, preferably up to 500, and more preferably from 10 to 250; m is zero or an integer with a value of from 1 to 10,000, preferably from 1 to 500 and more preferably from 1 to 250; R represents a divalent group containing up to 20 carbon atoms and includes substituted and unsubstituted alkylene, arylene, aralkylene, alkarylene, alkylenearylene, or divalent alicyclic or heterocyclic groups; R' represents a divalent group containing up to 20 carbon atoms, and includes alkylene, arylene, aralkylene, alkarylene, alkylenearylene, or divalent alicyclic or heterocyclic groups and $R_1$, $R_2$, $R_3$ and $R_4$ represent hydrogen, OH, F, Cl, Br, I, $NO_2$, NO, COOH, $SO_3H$, $NH_2$, $NHNH_2$, arylazo, heteroarylazo or a substituted or unsubstituted alkyl, aryl or heteroaryl group of up to 20 carbon atoms.

The terms "alicyclic" and "heterocyclic" as used throughout the specification and appended claims refers to monocyclic and polycyclic groups composed of hydrogen and up to 20 carbon atoms, more preferably up to 12, and which may also contain one or more heteroatoms such as oxygen, nitrogen or sulfur. Preferred are those groups containing up to 6 ring atoms.

The term "substituted" as used throughout the specification and appended claims refers to substituents such as lower alkyl or aryl of up to about 12 carbon atoms, halogen, hydroxyl, nitro, and the like.

The quinoline polymers of the present invention were synthesized by allowing 2-aminomethyl-8-hydroxyquinolines of the general formula:

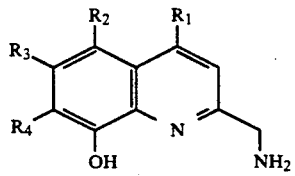

to react with diisocyanates of the general formula:

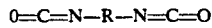

wherein R, $R_1$, $R_2$, $R_3$ and $R_4$ are as indicated above.

Examples of the quinolines which may be employed include 2-aminomethyl-4,8-dihydroxyquinoline, 2- aminomethyl-4,8-dihydroxy-5-phenylazoquinoline, and the like.

The diisocyanates which can be employed include, for example, polymethylenediisocyanates such as tetramethylenediisocyanate and hexamethylenediisocyanate, and aromatic diisocyanates such as 2,4-toluenediisocyanate, mixtures of 2,4-and 2,6-toluenediisocyanates (80/20:2,4/2,6); p,p'-diphenylenediisocyanate, p,p'-diphenylmethane diisocyanate, 3,3'-dimethoxy-4,4'-biphenylene diisocyanate, 3,3'-diphenyl-4,4'-biphenylene diisocyanate, 4-chloro-1,3-phenylene diisocyanate, 3,3'-dichloro-4,4'-biphenylene diisocyanate, 1,5-naphthlene diisocyanate, 1,5-tetrahydronaphthlene diisocyanate, and other polyisocyanates such as 4,4'-diphenylmethanediisocyanate, p-phenylenediisocyanates, 1,5-tetrahydronaphthalenediisocyanate and 4,4'-dicyclohexylmethanediisocyanate.

The solvents which may be employed include tetrahydrofuran, toluene, dimethylformamide, dimethylsulfoxide, acetone, pyridine, methylenechloride and dioxane with pyridine being the preferred solvent.

The temperature of the reaction ranges from about 0° to 150° C., with the preferred temperature being 80° C.

In general, it is preferred to employ stoichiometric equivalent amounts of the 2-amino-methyl-8-hydroxyquinoline and the diisocyanate although proportions of the quinoline and the diisocyanate may range from about 0.75:1 to 1.25:1.

An indirect route for the synthesis of quinoline copolymers involves the preparation of the 2-ureadomethyl-8-carbamatoquinolines bearing terminal isocyanato groups, as in the formula:

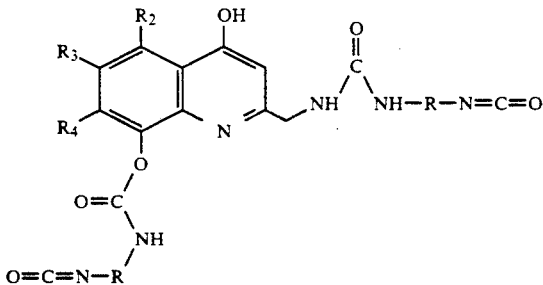

wherein R1-R4 are as previously described. The bisisocyanatoquinoline is then allowed to react with diamine compounds of the formula:

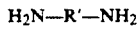

to provide quinoline copolymers of the general formula:

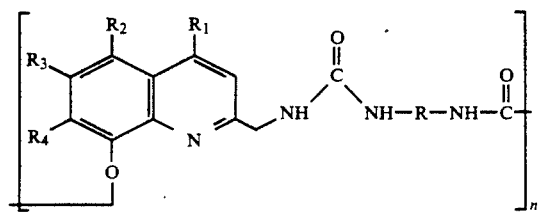

-continued

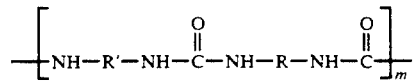

wherein R, R', $R_1$–$R_4$, n and m are as previously defined.

As indicated above, the quinoline polymers of the present invention complex with metal ions to form novel chelates. The choice of the particular metal ion will depend, of course, on the intended use of the chelate. That is, whether such use is in vitro or in vivo as well as the ability of the particular metal ion to form the chelate compound with the quinoline polymer of the invention.

Suitable metal ions include, but are not limited to, transition metal ions having atomic numbers of 21 to 29 and 40 to 83 and ions derived from the elements of the lanthanide series.

For nuclear therapy, one can use radioactive ions derived from elements such as copper, yttrium, rhenium, holmium, cesium and the like.

For fluorescence, one can utilize the elements of the lanthanide series such as europium, terbium, lanthanum and the like.

Preparation of the chelates of the quinoline polymers and the metal ions is effected in the conventional manner for the preparation of chelation of compounds. In practice, this can be accomplished by combining the quinoline polymer with an appropriate metal ion salt in an inert liquid medium. It is preferable to use a solvent in which both reaction partners are soluble. As shown in the examples, the quinoline polymer and the metal salts were mixed in an inert liquid, such as dimethylsulfoxide, and stirred at room temperature. The quinoline polymers of this invention are receptive to chelation, and thus may be advantageously utilized in any of the general technologies: radioisotopes for therapy and fluorescence in in vivo diagnostics, for example.

The following examples are illustrative of the best mode presently contemplated for the practice of this invention.

EXAMPLE 1

Polymer of 2-Aminomethyl-4,8-dihydroxyquinoline and 1,6-Diisocyanatohexane

A mixture of 238 milligrams (1.237 mmol) of 2-amino-4,8-dihydroxyquinoline and 0.2 milliliters (1.237 mmol) of 1,6-dissocyanatohexane in five milliliters of anydrous pyridine was stirred at 80° C. for four hours and at ambient temperature for 18 hours. Methanol (10 milliliters) was added and the solvents were removed by a rotary evaporator. The product was washed with methanol. 100 milligrams of the colorless solid polymer were obtained.

EXAMPLE 2

2-Ureadomethyl-4-hydroxy-8-carbamatoquinoline
Chemical Structure:

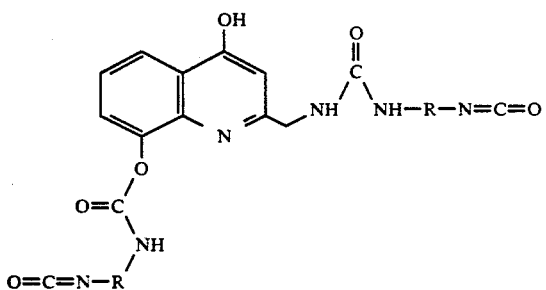

A mixture of 160 miligrams (0.84 mmol) of 2-aminomethyl 4,8-dihydroxyquinoline and 1.0 milliliters of 1,6-diisocyanatohexane in 2.5 milliliters of anhydrous pyridine was stirred at ambient temperature for four days. The solvent was removed under high vacuo and the produce washed several times with hexane to remove the excess diisocyanate. 600 milligrams of the product was obtained. TLC on silica gel plate, using 20% methanol-methylene chloride, showed one spot, $R_f 0.84$; infrared spectrum showed strong band at 2280 cm$^{-1}$ (—N=C=O ).

EXAMPLE 3

Quinoline-pyridine Copolymer

The product of Example 2 was redissolved in five milliliters of anhydrous pyridine, To this was added 74 millgrams of 2,6-diaminopyridine and the mixture was stirred at amient temperature for 18 hours. The reaction mixture was then stirred at 100° C. for two hours and allowd to cool to room temperature. The solvent was removed in a rotary evaporator and the produce was washed with methanol. 420 milligrams of the copolymer was obtained.

EXAMPLE 4

Labeling of Quinoline Polymer with Ytrium-90

5 milligrams of quinoline polymer prepared as in Example 1 were dissolved in 1 ml of dimethylsulfoxide. To this was then added 1 mCi of yttrium-90 acetate, and to the stirrred solution 1 ml of 0.01M tris uffer (pH 7) was added in order to precipitate the particles. After 30 minutes of incubation at ambient temperature, the particles were filtered using a membrane with a molecular weight cut off of 30,000 Daltons, and washed three times with the same buffer. The biodistribution study in rabbits was performed by resuspending these labeled particles in saline, injecting the suspended material into the synovial cavity, and analyzing the readioactivity uptake by various organs over various time periods postinjection.

EXAMPLE 5

Labeling of Quioline Polymer with Indium-111

2 Mg of quinoline polymer, prepared according to Example 1, were dissolved in 1 ml of dimethylsulfoxide, To this was added 0.3 mCi of indium-111 tropolone, the rest of the procedure is the same as that for the labeling yttrium-90 detailed in Example 4. The indium-111 labeled particles were resuspended in saline and used for i. v. administration in animals as in Example 4.

Although the invention has been illustrated by the preceding examples, it is not to be construed as being limited to the materials employed therein, but rather, the invention is directed to the generic area as hereinbefore disclosed. Various modifications and embodiments thereof can be made without departing from the spirit or scope thereof.

What is claimed is:

1. A quinoline polymer chelate comprised of:
(a) a quinoline polymer having the following recurring unit:

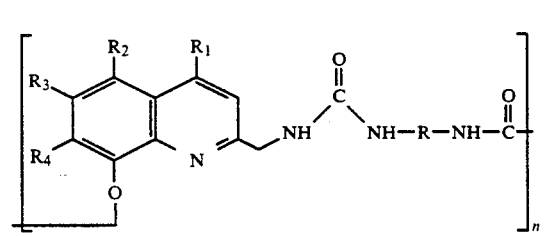

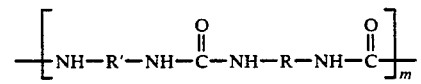

wherein n is an integer having a value of up to 10,000; m is zero or an integer with a value of from 1 to 10,000; R represents a divalent group containing up to 20 carbon atoms and may be substituted with alkylene, arylene, aralkylene, alkarylene, alkylenearylene, or divalent alicyclic or heterocyclic groups; R' represents a divalent group containing up to 20 carbon atoms, and represents alkylene, arylene, aralkylene, alkarylene, alkylenearylene, or divalent alicyclic or heterocyclic groups and $R_1$, $R_2$, $R_3$ and $R_4$ represent hydrogen, OH, F, Cl, Br, I, $NO_2$, NO, COOH, $SO_3H$, $NH_2$, $NHNH_2$, arylazo, heteroarylazo or a substituted or unsubstituted alkyl, aryl or heteroaryl group of up to 20 carbon atoms; and (b) a metal ion.

2. The quinoline polymer chelate of claim 1 wherein m is zero.

3. The quinoline polymer chelate of claim 1 wherein R and R' are alkylene and the remaining R groups are hydrogen.

4. The quinoline polymer chelate of claim 1 wherein R is arylene, R' is alkylene and the remaining R groups are hydrogen.

5. The quinoline polymer chelate of claim 1 wherein R is alkarylene, R' is alkylene and the remaining R groups are hydrogen.

6. The chelate of claim 1 wherein the metal ion is technetium 99m.

7. The chelate of claim 1 wherein the metal ion is indium.

8. The chelate of claim 1 wherein the metal ion is gallium.

9. The chelate of claim 1 wherein the metal ion is yttrium 90.

10. The chelate of claim 1 wherein the metal ion is holmium 166.

11. The chelate of claim 1 wherein the metal ion is rhenium 186.

12. The chelate of claim 1 wherein the metal ion is iron. lanthanum.

13. The chelate of claim 1 wherein the metal ion is gallium 67.

14. The chelate of claim 1 wherein the metal ion is indium 111.

15. The chelate of claim 1 wherein the metal ion is copper.

16. A pharmaceutical composition comprised of a therapeutically effective amount of the quinoline polymer chelate of claim 1 and a pharmaceutically acceptable carrier.

* * * * *